(12) United States Patent
Bernhardt et al.

(10) Patent No.: US 9,901,312 B2
(45) Date of Patent: Feb. 27, 2018

(54) MEDICAL INSTRUMENT FOR USE WITH A PHASE CONTRAST IMAGING AND X-RAY RECORDING SYSTEM WITH PHASE CONTRAST IMAGING

(71) Applicant: SIEMENS HEALTHCARE GMBH, Erlangen (DE)

(72) Inventors: Philipp Bernhardt, Forchheim (DE); Martin Hoheisel, Erlangen (DE); Thomas Mertelmeier, Erlangen (DE); Ralf Nanke, Neunkirchen am Brand (DE); Marcus Radicke, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 200 days.

(21) Appl. No.: 14/011,984

(22) Filed: Aug. 28, 2013

(65) Prior Publication Data
US 2015/0031986 A1    Jan. 29, 2015

(30) Foreign Application Priority Data
Jul. 23, 2013  (DE) .................... 10 2013 214 388

(51) Int. Cl.
*A61B 6/00* (2006.01)
*A61B 6/12* (2006.01)
(52) U.S. Cl.
CPC .............. *A61B 6/12* (2013.01); *A61B 6/4441* (2013.01); *A61B 6/484* (2013.01); *A61B 6/4458* (2013.01)
(58) Field of Classification Search
CPC ..... A61B 6/4441; A61B 6/484; A61B 6/4458; A61B 12/003; A61B 6/583; A61B 6/40; A61B 6/5235; A61B 6/4035; A61B 6/482; A61B 6/483; A61B 6/505; A61B 6/4241; A61B 6/4042; A61B 6/4291;
(Continued)

(56) References Cited

U.S. PATENT DOCUMENTS

| 4,146,793 A | * | 3/1979 | Bergstrom | ........... A61B 6/0428 378/161 |
| 6,081,739 A | * | 6/2000 | Lemchen | ............. A61B 5/0064 600/407 |
| 6,594,335 B2 | | 7/2003 | Davidson | |

(Continued)

FOREIGN PATENT DOCUMENTS

CN   101868182 A    10/2010
DE   102007038381 A1    2/2009
(Continued)

OTHER PUBLICATIONS

Pfeiffer F et al , "Hard X-ray dark-field imaging using a grating interferometer", in Nature Materials, vol. 7, pp. 134-137, doi 10 1038/nmat2096, Feb. 1, 2008.
(Continued)

*Primary Examiner* — Elmer Chao
(74) *Attorney, Agent, or Firm* — Laurence Greenberg; Werner Stemer; Ralph Locher

(57) ABSTRACT

A medical instrument is provided for use with a phase contrast imaging. The medical instrument includes at least one component, which has a strong small angle scattering of x-rays. Furthermore, a corresponding x-ray recording system with phase contrast imaging for recording an examination object may include such a medical instrument.

16 Claims, 3 Drawing Sheets

(58) Field of Classification Search
CPC .......... A61B 12/006; G01N 23/20075; G01N 23/087; G01N 2223/206; G21K 1/067; H05G 2/001
See application file for complete search history.

(56) References Cited

U.S. PATENT DOCUMENTS

| | | | |
|---|---|---|---|
| 7,500,784 B2 | 3/2009 | Grebner | |
| 8,864,780 B2* | 10/2014 | Euteneuer | A61F 2/0063 606/151 |
| 2006/0064064 A1* | 3/2006 | Jang | A61M 25/1002 604/194 |
| 2006/0292388 A1* | 12/2006 | Palumbo | A61F 2/82 428/586 |
| 2009/0257554 A1* | 10/2009 | Parks | A61B 6/12 378/44 |
| 2012/0224670 A1* | 9/2012 | Kiyohara | A61B 6/06 378/62 |

FOREIGN PATENT DOCUMENTS

| | | |
|---|---|---|
| DE | 102010018715 A1 | 11/2011 |
| WO | WO 2012104770 A2 | 8/2012 |

OTHER PUBLICATIONS

Martin Spahn, Flat detectors and their clinical applications Eur Radiol, vol. 15, pp. 1934-1947,, 2005, Apr. 2, 2005.

Zambelli Joseph et al , "Radiation dose efficiency comparison between differential phase contrast CT and conventional absorption CT", in Medical Physics, Jun. 2010, vol. 37, No. 6, pp. 2473-2479, DOI 10 1118/1 3425785.

Bech Martin et al, "Soft-tissue phase-contrast tomography with an x-ray tube source", Physics in medicine and biology, 2009, vol. 54, Issue 9, pp. 2747-2753, doi 10 1088/0031-9155/54/9/010.

Bech Martin et al , "Quantitative x-ray dark-field computed tomography", in Phys Med Biol , vol. 55, 2010, pp. 5529-5539, doi 10 1088/0031-9155/55/18/017.

* cited by examiner

MEDICAL INSTRUMENT FOR USE WITH A PHASE CONTRAST IMAGING AND X-RAY RECORDING SYSTEM WITH PHASE CONTRAST IMAGING

CROSS REFERENCE TO RELATED APPLICATIONS

This application claims priority of German Patent Office application No. 102013214388.5 DE filed Jul. 23, 2013. All of the applications are incorporated by reference herein in their entirety.

FIELD OF INVENTION

The present invention relates to a medical instrument for use with a phase contrast imaging. Furthermore, the present invention relates to a corresponding x-ray recording system with phase contrast imaging.

BACKGROUND OF INVENTION

The differential phase contrast imaging or in short phase contrast imaging represents an imaging method which has received a lot of attention over the last few years particularly in the Talbot Lau interferometer arrangement. The publication by F. Pfeiffer et al., "Hard X-ray dark-field imaging using a grating interferometer", Nature Materials 7, pages 134 to 137 describes that with the aid of an interferometric structure, which consists of a conventional x-ray tube, three gratings and an x-ray detector, both absorption contrast, differential phase contrast and also dark-field contrast can be reconstructed from the same data record. The same can also be inferred from Joseph J. Zambelli, et al., "Radiation dose efficiency comparison between differential phase contrast CT and conventional absorption CT", Med. Phys. 37 (2010), pages 2473 to 2479, or Bech et al., "Soft-tissue phase-contrast tomography with an x-ray tube source", Phys. Med. Biol. 54 (2009), pages 2747 to 2753, or Bech et al, "Quantitative x-ray dark-field computed tomography", Physics in Medicine an Biology, 55:5529-5539, 2010.

The wave nature of particles such as x-ray quanta allows for the description of phenomena such as refraction and reflection with the aid of the complex refractive index $$n = 1 - \delta + i\beta.$$

Here the imaginary part $\beta$ describes the absorption, which forms the basis of current clinical x-ray imaging, such as for instance computed tomography, angiography, radiography, fluoroscopy or mammography, and the real part $\delta$ describes the phase displacement which is observed during the differential phase contrast imaging.

DE 10 2010 018 715 A1 discloses an x-ray recording system, in which an x-ray recording system is used for phase contrast imaging of an examination object for the purpose of high-quality x-ray imaging, said x-ray recording system comprising at least one x-ray emitter with a plurality of field emission x-ray sources for emitting coherent x-rays, an x-ray detector, a diffraction grating $G_1$ arranged between the examination object and the x-ray image detector and a further grating $G_2$ which is arranged between the diffraction grating $G_1$ and the x-ray image detector.

In the arrangements currently the focus of attention for clinical phase contrast imaging, conventional x-ray tubes, currently available x-ray image detectors, such as described for instance by M. Spahn in "Flat detectors and their clinical applications", European Radiology, Volume 15 (2005), pages 1934 to 1947, and three gratings $G_0$, $G_1$ and $G_2$ are used, such as is subsequently explained in more detail with the aid of FIG. 1, which indicates a schematic structure of a Talbot Lau interferometer for the differential phase contrast imaging with extended tube focus, gratings $G_0$, $G_1$ and $G_2$ and a pixelated x-ray image detector.

The x-rays 12 originating from a tube focus 11 of a non-coherent x-ray emitter 32 penetrate an absorption grating ($G_0$) in order to generate coherent radiation, said absorption grating effecting the local coherence of the x-ray source, and an examination object 6, for instance a human or animal patient. The wave front of the x-rays 12 through the examination object 6 is deflected by phase displacement such that, such as the normal 15 of the wave front without phase displacement, i.e. without object, and the normal 16 of the wave front with phase displacement indicate. The phase-displaced wave front then passes through a diffraction or phase grating 17 ($G_1$) with a grating constant adjusted to the typical energy of the x-ray spectrum in order to generate interference lines and/or an interference pattern 18 and in turn an absorbing analyzer grating 19 ($G_2$) for reading out the generated interference pattern 18. Different interference patterns 18 develop with and without an object. The grating constant of the analyzer grating 19 is adjusted to that of the phase grating 17 and the remaining geometry of the arrangement. The analyzer grating 19 is for instance arranged at the first or n'th Talbot distance (order). The analyzer grating 19 in this way converts the interference pattern 18 into an intensity pattern, which can be measured by a detector or x-ray image detector 4. Typical grating constants for clinical applications are in the order of a few µm, as is also inferred for instance from the cited citations.

If the x-ray source is sufficiently coherent, i.e. the tube focus 11 of the x-ray source is sufficiently small and the generated x-ray power is consequently sufficiently large, it is possible to dispense with the first grating $G_0$, the absorption grating 13.

The differential phase displacement is now determined for each pixel of the x-ray image detector 4 according to the prior art such that by means of a so-called "phase stepping" 20, which is indicated by an arrow, the analyzer grating 19 ($G_2$) is displaced in a number of steps (k=1, ... K, with e.g. K=4 to 8) by a corresponding fraction of the grating constant at right angles to the beam direction of the x-rays 12 and laterally with respect to the arrangement of the grating structure and the signal $S_k$ produced for this configuration during the recording is measured in the pixel of the x-ray image detector 4 and the produced interference pattern 18 is thus scanned. For each pixel, the parameters of a function describing the modulation (e.g. sinus function) are then determined by a suitable fit method, an adjustment or compensation method, on the thus measured signals $S_k$. These parameters are usually the amplitude A, the phase $\Phi$ and the average intensity I.

Three different images can then be generated from the comparison of certain derived variables from these fit parameters for each pixel once with and once without an examination object, i.e. patient:

absorption image,
differential phase contrast image (DPC) and
dark-field image.

In other words, with dark-field images, the local, i.e. within a pixel, destruction of the coherence of the x-rays is imaged. According to current knowledge scatter centers below the actual system resolution contribute significantly to this effect. With the grating-based phase contrast imaging, an absorption contrast, phase contrast and dark-field image are simultaneously obtained.

The visibility, i.e. the standardized difference from the maximum and minimum signal (or more precisely: amplitude standardized to the average signal), is here a measure of the characterization of the quality of a Talbot Lau interferometer. It is defined as a contrast of the scanned modulation $$V = \frac{I_{max} - I_{min}}{I_{max} + I_{min}} = \frac{A}{I}.$$

Where an image is mentioned below, the triumvirate of absorption, DPC and dark-field image is meant where applicable.

With clinical interventions, auxiliary objects or medical instruments are inter alia introduced into the human body during surgery or orthopedics. In conventional medical x-ray based imaging, these medical instruments, such as for instance guide wires, stents, catheters etc., in the further sense also contrast agent, are made visible with the aid of the absorption contrast, i.e. x-rays are more significantly absorbed on these objects than in the remaining body, thereby indicating a signal difference on a locally resolved detector. The position of these objects is to be controlled in many instances as easily as possible and with a low x-ray dose. In order to be able to display these objects with a good contrast, they are usually manufactured from materials which contain elements with a high harmonic order, such as for instance metals. In order to further increase the visibility of these objects, they are often provided with additional materials with a high absorption. Markers comprising a platinum-iridium alloy are thus applied for instance to guide wires or medical plastics for catheters are also enriched with barium sulphate. A medical adhesive, for instance onyx, is mentioned as a further example, which is mixed with fine tantalum powder, in order to render the same visible in the x-ray image.

As described previously, another method of rendering visible structures in the human body with the aid of x-rays relates to the phase contrast imaging and/or x-ray dark-field images, which primarily do not use the absorbing effect of the material on x-rays, but instead the effect of the phase displacement when passing through the object and/or the refraction of the x-rays when transmitting refractive index gradients. If the medical instruments proven in use with classical x-ray technology are used with a phase contrast imaging, the achieved results, in particular with respect to the display quality of the obtained x-ray images, are often inadequate.

SUMMARY OF INVENTION

The object of the present invention now consists in specifying a medical instrument, which is particularly suited to use with a phase contrast imaging and is characterized in particular compared with conventional medical instruments by an improved visibility in a differential phase contrast image and/or dark-field image. The object of the present invention further consists in specifying a corresponding x-ray recording system.

The above objects are achieved by the features of the independent claim(s). Advantageous embodiments are described in the subclaims.

A basic idea of the invention is a medical instrument for use with a phase contrast imaging, which is characterized in that the medical instrument includes at least one component which exhibits a strong small angle scattering of x-rays.

A medical instrument may for instance be a medical tool for an interventional operation on a patient or for a diagnostic examination of a patient. The medical instrument is suited to use with a phase contrast imaging, i.e. with a means which allows for imaging using phase contrast. The inventive medical instrument includes at least one component which exhibits a strong small angle scattering of x-rays. The complete instrument can thus also exhibit a strong small angle scattering of x-rays. Or the component can be a region of the instrument, into which the material is integrated, or is a discrete component which is connected to a conventional medical instrument. A transition is also conceivable, continuously or staged, of the strength of the small angle scattering within a component, i.e. a material or a material arrangement comprising a gradient of the refractive index.

A strong small angle scattering of x-rays indicates a strong small angle scattering compared with currently conventional medical instruments. The stronger small angle scattering of the inventive medical instrument increases the contrast of the inventive medical instrument in a dark-field image such that the visibility of the inventive medical instrument is improved by comparison with a present-day conventional medical instrument. Conversely, medical instruments can be configured such that they are easily visible in the dark-field, in the absorption image, i.e. in classic x-ray technology, but are not visible, and in the extreme case, in particular no metal artifacts appear either. Better diagnostic possibilities result herefrom.

The medical instrument can preferably be introduced into an examination object or the medical instrument can be placed in an examination object.

If a medical instrument is introduced into an examination object, e.g. a human or animal patient, the medical instrument is already inserted into an examination object or is placed in an examination object, it can be withdrawn from direct observation by a physician for instance. In these cases, imaging by means of x-ray technology is particularly advantageous, particularly if it involves a phase contrast imaging with an inventive medical instrument.

This can also be auxiliary means, which can be introduced into a patient, and can remain temporarily or indefinitely in a patient, such as for instance a prosthesis or an angioplasty stent.

It is proposed that the medical instrument includes a guide wire, a stent or a catheter.

The cited medical instruments are used in many instances in minimally invasive interventions, which in principle feature a restricted visibility after introduction into an examination object so that a phase contrast imaging can be advantageously used with an inventive medical instrument.

In an advantageous development, the at least one component of the medical instrument comprises a microstructure.

A microstructure is understood in material science to mean the microscopic composition of a material. By means of a suitable molding of the surface or at least a subvolume of the medical device, the visibility in an image, which has been obtained with the aid of phase contrast imaging, can be maximized or at least improved.

In a further advantageous embodiment, the at least one component of the medical instrument comprises a microstructure with a predeterminable structure size.

The structure size, i.e. the dimensions of the microscopic constituents of the components of the material, can be adjusted for instance to the grating constant of an analyzer grating and/or to those of the phase grating and/or to the remaining geometry of the arrangement.

The predeterminable structure size of the at least one component of the medical instrument advantageously amounts to between 0.01 μm and 100 μm.

A high image contrast by means of small angle scattering can be achieved by micro structures with structure sizes between 0.01 μm and 100 μm. Structures within the medical instrument and/or a non-smooth surface of the medical instrument, which comprise a structure size between 10 μm and 50 μm, provide a high dark-field sensitivity and thus a high image contrast particularly in the field of mammography.

It has proven advantageous if the microstructure of the at least one component of the medical instrument is formed by a fibrous or porous material.

Porous material, i.e. a material having pores, can be understood for instance to mean a spongy or foam-type material with a solid or flexible consistency. The diameter of the pores can herewith determine the structure size of the material. The spacing of the pores can also be interpreted as a structure size. A fibrous material can be understood to be a material comprising fibers. A fiber is generally a thin and flexible structure in relation to its length, wherein materials with rigid fibers are also conceivable. The diameter of a fiber can determine the structure size of the material.

A preferred embodiment of a basic idea of the invention provides for the porous material of the at least one component of the medical instrument to have a closed porosity and for at least part of the pores to include a predeterminable material.

A closed porosity can advantageously be formed by a foam-type material. Foam is understood usually to mean a plurality of gaseous bubbles, which are enclosed by fixed, liquid or flexible walls. An inventive medical instrument could thus include a structure, e.g. by means of a superficial layer or an inner volume, from foam made up of gas bubbles, wherein the gas bubbles advantageously each exhibit a diameter in the range of 0.01 μm to 100 μm.

A further advantageous embodiment provides that the fibrous material of the at least one component of the medical instrument includes a carbon fiber-reinforced plastic.

Carbon fibers are industrially manufactured fibers made of carbon-containing raw materials, which are converted by prolepsis into graphite-type carbon and are much used in technology. It would be conceivable to apply carbon fibers individually or in bundles and embedded in plastic onto the surface of a medical instrument, in order thus to achieve a structure size which is easily identifiable in a dark field.

A further basic idea of the invention is an x-ray recording system having phase contrast imaging for recording an examination object and a medical instrument. The x-ray recording system includes an x-ray device for capturing x-ray images of an examination object by means of direct measurement of an interference pattern, having at least one x-ray emitter for generating almost coherent x-rays, an x-ray image detector, which comprises a detector layer and detector pixels arranged in a matrix, a diffraction or phase grating, which is arranged between the examination object and the x-ray image detector and an interference pattern, wherein the medical instrument includes at least one component, which has a strong small angle scattering of x-rays.

The medical instrument of the x-ray recording system is particularly advantageously embodied according to a previously described, inventive embodiment.

The exemplary embodiments shown in more detail below represent preferred embodiments of the present invention.

BRIEF DESCRIPTION OF THE DRAWINGS

Further advantageous developments result from the subsequent figures including the description, in which.

DETAILED DESCRIPTION OF INVENTION

Figure 1:
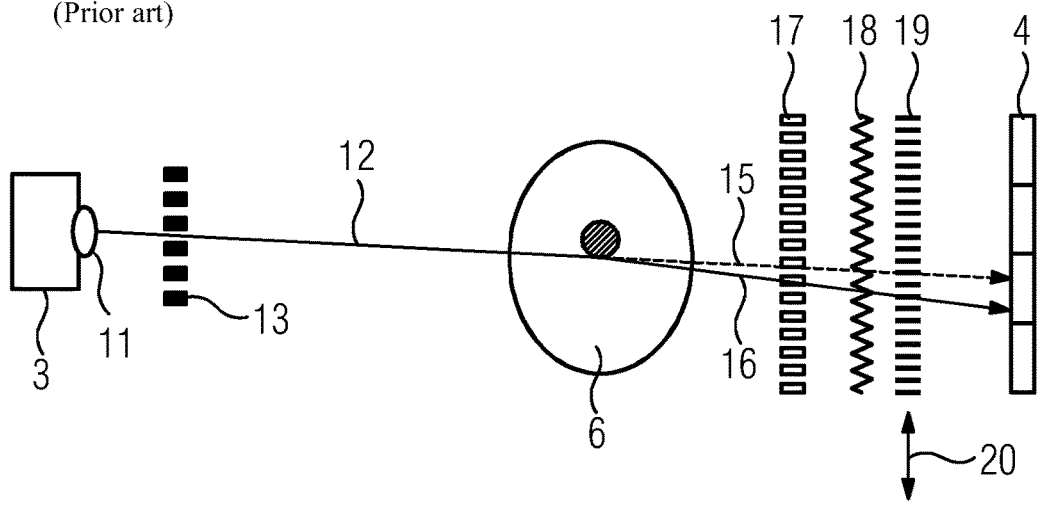
FIG. 1 shows a schematic structure of a known Talbot Lau interferometer for the differential phase contrast imaging with an extended tube focus, three gratings $G_0$, $G_1$ and $G_2$ and a pixelated detector.
Figure 2:
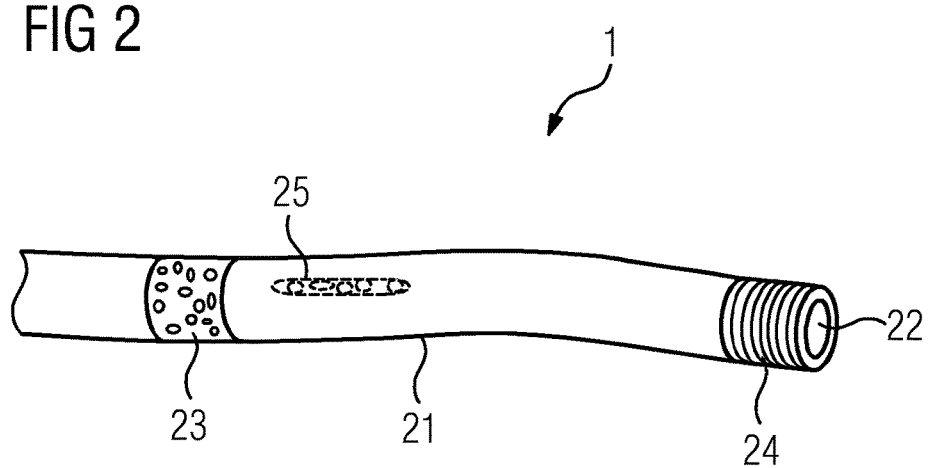
FIG. 2 shows a schematic representation by way of example of a medical instrument having a number of components, which enable a good x-ray dark-field image representation.

FIG. 2 by way of example shows a schematic medical instrument 1 having a number of components which enable a good x-ray dark-field image representation. The medical instrument 1 is embodied as a medical catheter. A medical catheter is understood to mean in particular a tubular or rod-type device with a length of approx. 0.3 to 1.5 m and a diameter of approx. 1 to 20 mm, which can be introduced into a human or animal body. Furthermore, a medical catheter can include integrated instruments which can be introduced by way of working channels, e.g. micromechanical devices, such as small forceps or grippers, with which examining or intervening procedures can be performed. The medical instrument 1 includes a tubular base body 21, which has an opening 22. A first subarea 23 of the tubular base body 21 is embodied with a layer of sponge-type material, so that the surface of this region has microscopically small, porous openings, which can be effectively displayed, in particular in a contrast-rich fashion, in a dark-field image, with the aid of an x-ray dark-field imaging. A second subarea 24 includes a tubular section, which consists of a carbon fiber-reinforced plastic. A suitable selection of the structure, the structure size and the structure extension allows the intensity and the spatial extension of the dark-field signal to be directly influenced in the image. The region 24 of the medical instrument can thus be shown more precisely and in suitable instances also with a lower x-ray dose, than by means of conventional x-ray imaging. A third subarea 25 of the tubular base body 21 includes a foam-type structure inside the tubular base body 21, which likewise effects a large dark-field signal. By means of longitudinal formation of the foam-type region it is possible to deduce the alignment of the medical instrument on a dark-field image, as a result of which detection of a 2D/3D orientation of the medical instrument in the x-ray image is possible for instance.

Figure 3:
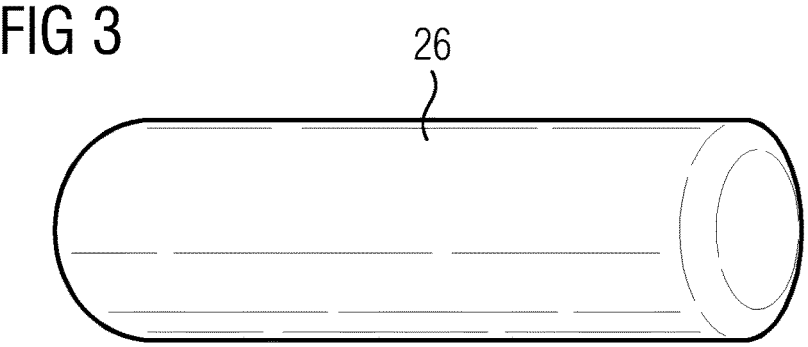
FIG. 3 shows an embodiment of a medical instrument having a sponge-type surface.

FIG. 3 shows a schematic representation of an embodiment of a medical instrument 26 having a sponge-type surface. A contrast-rich imaging of the medical instrument on a dark-field image is possible due to the structure of the surface, which is characterized by microscopically small openings, for instance with diameters in the micrometer range.

Figure 4:
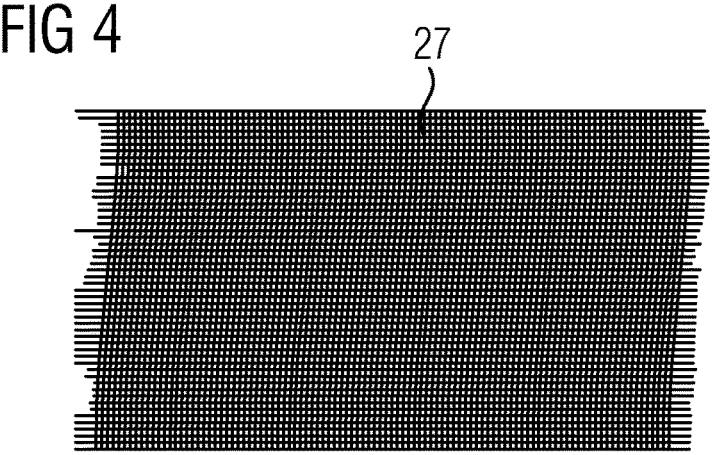
FIG. 4 shows an embodiment of a fibrous surface of a medical instrument.

FIG. 4 shows a schematic representation of an embodiment of a fibrous surface 27 of a medical instrument. The fibers of the fibrous surface are arranged in a network adjacent to one another or in the manner of a fabric and can be fixed on the medical instrument by means of a plastic substrate. The diameter of a fiber, which advantageously lies in the micrometer range, determines the structure size of the surface and thus the intensity and the spatial extent of the dark-field signal in the dark-field image.

Figure 5:
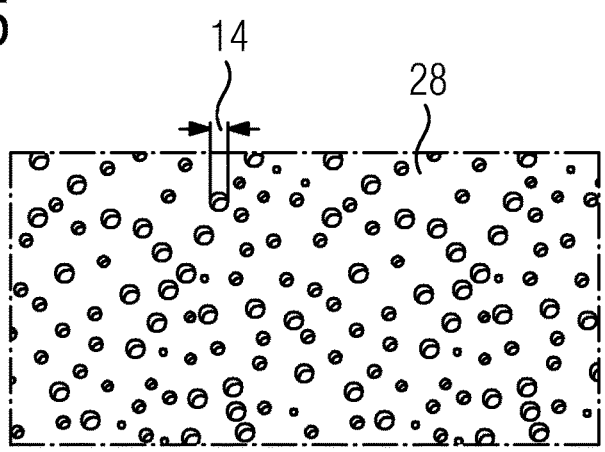
FIG. 5 shows an embodiment of a foam-type surface of a medical instrument.

FIG. 5 shows a schematic representation of an embodiment of a foam-type surface 28 of a medical instrument. The foam-type surface 28 is formed by a foam made up of gas bubbles. The foam can be applied for instance as a thin, e.g. less than one millimeter thick, film onto the medical instrument. During mammography, these gas bubbles could exhibit a diameter 14 in the range of 10 µm to 50 µm respectively for instance. The diameter of the gas bubbles, and if necessary their spacing from one another, determine the microstructure of the surface 28.

Figure 6:
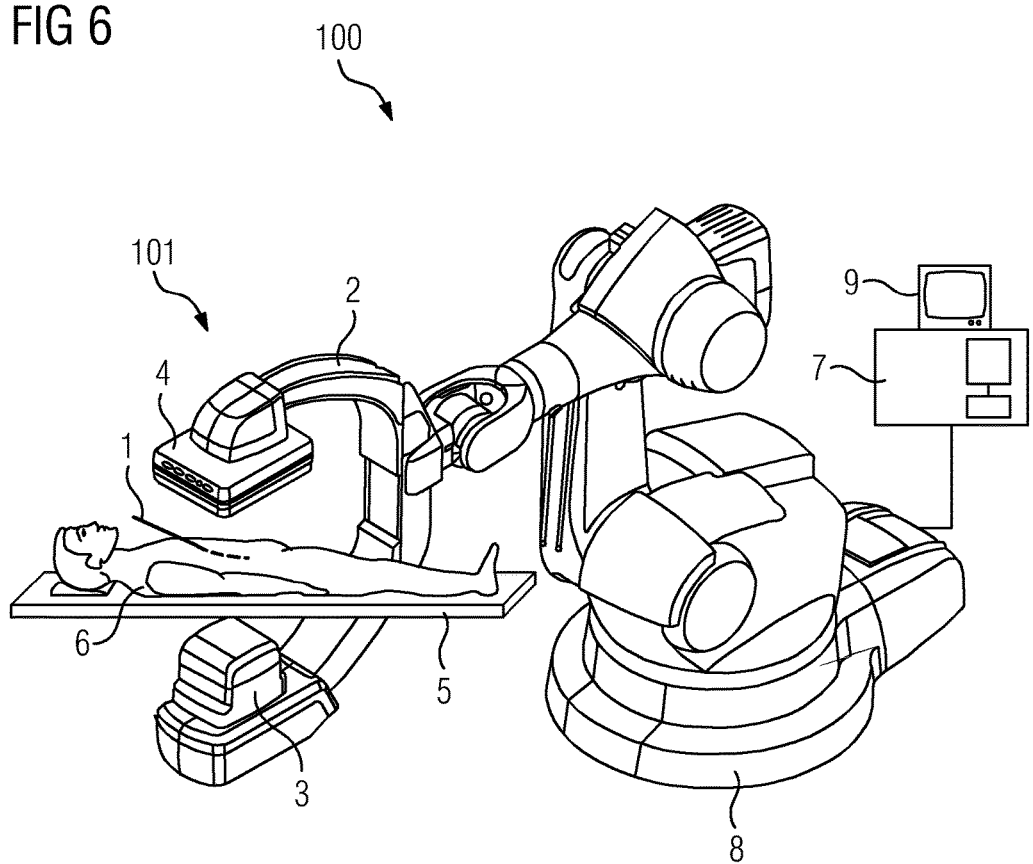
FIG. 6 shows a schematic exemplary embodiment of an x-ray recording system with phase contrast imaging for recording an examination object and a medical instrument.

FIG. 6 shows a schematic exemplary embodiment of an x-ray recording system 100 having phase contrast imaging for recording an examination object 6 and a medical instrument 1. The x-ray recording system 100 includes an x-ray device 101 for x-ray imaging by means of—phase contrast imaging and a medical instrument 1, which includes at least one component, comprising a strong small angle scattering of x-rays. The x-ray device 101 is equipped with a C-arm 2 held by a stand 8 in the form of a six-axis industrial and articulated arm robot, to the ends of which an x-ray source, for instance an x-ray emitter 3 with x-ray tube and collimator, and an x-ray image detector 4 are attached as the image recording unit.

The C-arm 2 can be arbitrarily spatially adjusted, for instance by being rotated about a center of rotation between the x-ray emitter 3 and the x-ray image detector 4, by means of the articulated arm robot known from U.S. Pat. No. 7,500,784 B2 for instance, which preferably has six axes of rotation and thus six degrees of freedom. The realization of the x-ray device 101 does not rely on the industrial robot. Conventional C-arm devices can also be used.

The x-ray image detector 4 may be a rectangular or square, planar x-ray detector, which is preferably made up of a scintillator (e.g. CsJ) and an active matrix made of photodiodes from amorphous silicon (a-Si). Integrating detectors based on CMOS or also counting detectors (e.g. CdTe or CZT or ASIC) can however also be used. The x-ray image detector 4 thus comprises a detector layer and detector pixels arranged in a matrix.

A patient to be examined as an examination object 6 is disposed in the beam path of the x-ray emitter 3 on a couch 5 of a patient support couch. A system control unit 7 with an imaging system 9 is connected to the x-ray diagnostic facility, said imaging system receiving and processing the image signals of the x-ray image detector 4, wherein control elements are not shown for instance. The x-ray images obtained can then be observed on the imaging system 9, which can be embodied for instance as a monitor signal system with a number of monitors.

The medical instrument 1 is embodied as a catheter in this exemplary embodiment, which can be introduced into the examination object 6. The medical instrument 1 of the exemplary embodiment includes a component, having a strong small angle scattering of x-rays. In particular, the component of the medical instrument 1 comprises a microstructure with a predeterminable structure size, e.g. a structure size between 10 µm and 50 µm, which is formed by a fibrous material, such as carbon fiber-reinforced plastic, or by a porous material, such as foam-type or sponge-type material.

In summary, further embodiments and advantages of the invention are described.

The phase contrast method has proven to be particularly attractive if it succeeds in representing medical instruments, the mapping of which was previously only possible with difficulty due to their low image contrast. This was the case for instance with very thin guide wires or with catheters consisting of plastic. It is proposed in this invention not to manufacture medical instruments, as previously usual, from highly absorbent materials, but instead to develop the same from sponge-type, foam-type or fibrous structures or to mark the same with such a material. In other words, the medical instruments exhibit a special surface or interior structure. Alternatively, material arrangements are to be used, which comprise the gradients of the refractive index. With such structures, a high degree of visibility of the correspondingly equipped instruments is obtained in the phase contrast image and/or in the dark-field image. With the embodiment of guide wires, stents and catheters according to the invention comprising sponge-type, or fibrous materials, these provide a high signal in the dark-field and can thus be recognized easily. In other words, dark-field images, in comparison with absorption and phase contrast, are sensitive to structures of the surface, of an inner structure of generally part of an object which lie below the system resolution. This essentially different sensitivity offers great potential for the visibility and thus the control of auxiliary objects within the human body, if these auxiliary objects are designed accordingly.

With the aid of the structure, the structure size and the structure extent, the intensity and the spatial extent of the dark-field signal can be directly influenced in the image. The corresponding instruments can thus be detected more precisely and in suitable instances also with a lower x-ray dose than previously. It is possible for instance that a very high x-ray energy is used for control purposes and thus the dose can be kept very low.

In accordance with the invention, embodiments of medical instruments can be configured for instance such that they are not visible in the absorption image, meaning in the extreme case that no metal artifacts appear for instance but can be easily seen in the dark-field. Better diagnostic possibilities result herefrom.

An overlay and/or registration of a dark-field image obtained with the aid of an inventive medical instrument with previously recorded image are possible, wherein control images can be recorded with a lower dose.

It would also be conceivable to attach a type of barcode comprising a dark-field signal to a medical instrument.

The structure of the dark-field generating components can be composed such that a detection of a 2D/3D orientation of medical instrument in the x-ray image is possible.

An exemplary embodiment of an inventive instrument is a guide wire, which is manufactured from a carbon fiber-reinforced plastic, in short CFRP. CFRP fibers of this type have a high stability. The fiber structure of the CFRP causes a guide wire produced in this way to generate a high dark-field signal and it is as result easily visible, whereas the current guide wires made of nitinol or stainless steel are often poorly visible since they are also very thin.

Alternatively, a combination comprising the conventional guide wire and the CFRP fiber can also be used, thus for instance a CFRP fiber which is covered by a metal such as nitinol or stainless steel for instance, or a metallic guide wire, which is encased with CFRP.

A further inventive application includes stents made of CFRP or other stable and biocompatible fibers, which can also be combined with nitinol or stainless steel wires. Stents of this type could replace the current stents consisting solely of nitinol or stainless steel and are thus significantly more visible in the dark-field image.

Catheters comprising a plastic set with microscopically small air bubbles can be produced as a further exemplary embodiment and as a result emit a clear signal in the dark-field image.

Alternatively, catheters with CFRP fibers can be provided in order to improve their visibility in the dark-field image.

The invention claimed is:

1. A medical instrument for use with a phase contrast imaging, comprising:
    at least one component which enables an x-ray image representation,
    the at least one component including a tubular base body having a surface;
    the tubular base body including a first subarea on a region of the surface that is embodied with a layer of spongy material, the spongy material including microscopically small porous openings with diameters in the micrometer range defining a structure of the first subarea;
    the tubular base body including a second subarea on another region of the surface that is embodied with a layer of carbon fiber-reinforced plastic material defining a structure of the second subarea;
    the tubular base body including a third subarea inside the tubular base body that is embodied with a foam material, the foam material including a plurality of gas bubbles defining a structure of the third subarea; and
    wherein the structure of each of the first subarea, the second subarea and the third subarea provides a degree of visibility of the medical instrument in the phase contrast imaging.

2. The medical instrument as claimed in claim 1, wherein the medical instrument can be introduced into an examination object or can be placed in an examination object.

3. The medical instrument as claimed in claim 1, wherein the medical instrument includes a guide wire, a stent or a catheter.

4. The medical instrument as claimed in claim 1, wherein the at least one component of the medical instrument comprises a microstructure.

5. The medical instrument as claimed in claim 4, wherein the at least one component of the medical instrument comprises the microstructure with predeterminable structure size.

6. The medical instrument as claimed in claim 5, wherein the predeterminable structure size of the at least one component of the medical instrument amounts to between 0.01 μm and 100 μm.

7. The medical instrument as claimed in claim 5, wherein the microstructure of the at least one component of the medical instrument is formed by a fibrous or porous material.

8. The medical instrument as claimed in claim 7, wherein the porous material of the at least one component of the medical instrument comprises a closed porosity and at least part of the pores includes a predeterminable material.

9. An x-ray recording system having phase contrast imaging for recording an examination object and a medical instrument, comprising:
    an x-ray device for x-ray imaging of an examination object by means of direct measurement of an interference pattern using at least one x-ray emitter for generating x-rays,
    an x-ray image detector, comprising a detector layer and detector pixels arranged in a matrix,
    a diffraction or phase grating, which is arranged between the examination object and the x-ray image detector and generates an interference pattern,
    wherein the medical instrument includes at least one component which enables an x-ray dark-field image representation,
    wherein the at least one component includes a tubular base body having a surface,
    the tubular base body including a first subarea on a region of the surface that is embodied with a layer of spongy material, wherein the spongy material includes microscopically small porous openings with diameters in the micrometer range defining a structure of the first subarea;
    the tubular base body including a second subarea on another region of the surface that is embodied with a layer of carbon fiber-reinforced plastic material defining a structure of the second subarea;
    the tubular base body including a third subarea inside the tubular base body that is embodied with a foam material including a plurality of gas bubbles defining a structure of the third subarea; and
    wherein the structure of each of the first subarea, the second subarea and the third subarea provides a degree of visibility of the medical instrument in the phase contrast imaging.

10. The x-ray recording system as claimed in claim 9, wherein the medical instrument can be introduced into an examination object or can be placed in an examination object.

11. The x-ray recording system as claimed in claim 9, wherein the medical instrument includes a guide wire, a stent or a catheter.

12. The x-ray recording system as claimed in claim 9, wherein the at least one component of the medical instrument comprises a microstructure.

13. The x-ray recording system as claimed in claim 12, wherein the at least one component of the medical instrument comprises the microstructure with predeterminable structure size.

14. The x-ray recording system as claimed in claim 13, wherein the predeterminable structure size of the at least one component of the medical instrument amounts to between 0.01 μm and 100 μm.

15. The x-ray recording system as claimed in claim 13, wherein the microstructure of the at least one component of the medical instrument is formed by a fibrous or porous material.

16. The x-ray recording system as claimed in claim 15, wherein the porous material of the at least one component of the medical instrument comprises a closed porosity and at least part of the pores includes a predeterminable material.

* * * * *